(12) United States Patent
 Xie et al.

(10) Patent No.: US 12,629,628 B2
(45) Date of Patent: May 19, 2026

(54) HOUSEHOLD OXYGEN GENERATOR

(71) Applicant: SHENZHEN HARVEYMED TECHNOLOGY CO., LTD., Shenzhen (CN)

(72) Inventors: Bangping Xie, Shenzhen (CN); Hanqing Chen, Shenzhen (CN); Haonan Fan, Shenzhen (CN)

(73) Assignee: Shenzhen Harveymed Technology Co., LTD., Shenzhen (CN)

( * ) Notice: Subject to any disclaimer, the term of this patent is extended or adjusted under 35 U.S.C. 154(b) by 0 days.

(21) Appl. No.: 19/106,470

(22) PCT Filed: Aug. 26, 2024

(86) PCT No.: PCT/CN2024/114446
 § 371 (c)(1),
 (2) Date: Feb. 25, 2025

(87) PCT Pub. No.: WO2025/148333
 PCT Pub. Date: Jul. 17, 2025

(65) Prior Publication Data
 US 2026/0042051 A1 Feb. 12, 2026

(30) Foreign Application Priority Data
 Jan. 10, 2024 (CN) .......................... 202420062807.7

(51) Int. Cl.
 *B01D 53/04* (2006.01)
 *A61M 16/10* (2006.01)
 (Continued)

(52) U.S. Cl.
 CPC ......... *B01D 53/0415* (2013.01); *B01D 53/02* (2013.01); *B01D 53/0446* (2013.01);
 (Continued)

(58) Field of Classification Search
 None
 See application file for complete search history.

(56) References Cited

U.S. PATENT DOCUMENTS

2023/0120349 A1* 4/2023 Hirai .................... B01D 53/053
 96/130

FOREIGN PATENT DOCUMENTS

CN 213375841 U 6/2021
CN 105069064 A 9/2022
 (Continued)

OTHER PUBLICATIONS

JP2014136134A_ENG (Espacenet machine translation of Hirose) (Year: 2014).*
 (Continued)

*Primary Examiner* — Gabriel E Gitman
(74) *Attorney, Agent, or Firm* — FBT Gibbons, LLP; Nicole Tepe, Esq.

(57) ABSTRACT

Provided is a household oxygen generator. The household oxygen generator includes a housing. A compression mechanism, a first air path module and an oxygen generation mechanism which are communicated in sequence are disposed in the housing. The first air path module includes a flow guide pipeline, a movable pipeline and a locking assembly. The movable pipeline is movably connected to the flow guide pipeline. The locking assembly is in transmission connection with the movable pipeline. The flow guide pipeline is connected to the oxygen generation mechanism. The locking assembly has a locking position and an unlocking position. When the locking assembly is in the locking position, the movable pipeline is clamped to or inserted into an air inlet of the oxygen generation mechanism. When the (Continued)

locking assembly is in the unlocking position, the movable pipeline is separated from the air inlet of the oxygen generation mechanism.

15 Claims, 5 Drawing Sheets

(51) Int. Cl.

| | | |
|---|---|---|
| B01D 53/02 | (2006.01) | |
| B01D 53/047 | (2006.01) | |
| C01B 13/02 | (2006.01) | |

(52) U.S. Cl.
CPC ........ *B01D 53/047* (2013.01); *C01B 13/0259* (2013.01); *A61M 16/101* (2014.02); *B01D 53/0407* (2013.01); *B01D 2221/08* (2013.01); *B01D 2256/12* (2013.01); *B01D 2259/4533* (2013.01); *B01D 2259/4541* (2013.01); *C01B 2210/0046* (2013.01)

(56) References Cited

FOREIGN PATENT DOCUMENTS

| | | | |
|---|---|---|---|
| CN | 217549425 | U | 10/2022 |
| CN | 116764382 | A | 9/2023 |
| JP | 2014136134 | A * | 4/2014 |
| WO | 2023133383 | A2 | 7/2023 |

OTHER PUBLICATIONS

International Search Report for PCT/CN2024/114446 mailed Nov. 19, 2024.

Written Opinion dated Nov. 19, 2024, for International Application No. PCT/CN2024/114446, 7 pages.

* cited by examiner

HOUSEHOLD OXYGEN GENERATOR

CROSS-REFERENCE TO RELATED APPLICATIONS

This is a national stage application filed under 37 U.S.C. 371 based on International Patent Application No. PCT/CN2024/114446, filed Aug. 26, 2024, which claims priority to Chinese Patent Application No. 202420062807.7, filed with the China National Intellectual Property Administration (CNIPA) on Jan. 10, 2024, the disclosures of which are incorporated herein by reference in their entireties.

TECHNICAL FIELD

The present application relates to the technical field of household oxygen generators, and in particular, to a household oxygen generator.

BACKGROUND

With the development of society, the number of the elderly population is gradually increasing, and diseases such as chronic obstructive pulmonary disease, heart disease, pulmonary fibrosis, and asthma are also increasing accordingly. However, these diseases are effectively alleviated and treated through oxygen inhalation.

With the improvement of medical standards and the deepening of people's understanding of diseases, more and more people are increasingly focusing on family healthcare, and thus an oxygen generation device is gradually becoming popular. After the oxygen generation device has been used for a period of time, an oxygen generation adsorbent needs to be replaced to ensure the quality of oxygen generation. However, the replacement of the oxygen generation adsorbent in the conventional household oxygen generation device is quite cumbersome, and it often requires complicated disassembly and mounting processes of pipelines, which increases the difficulty for non-professionals to disassemble, mount and replace the oxygen generation adsorbent by themselves.

SUMMARY

The present application provides a household oxygen generator to solve the problem of the relatively high difficulty in disassembling and replacing the oxygen generation adsorbent.

A household oxygen generator according to the present application includes a housing. A compression mechanism, a first air path module and an oxygen generation mechanism which are communicated in sequence are disposed in the housing. The first air path module includes a flow guide pipeline, a movable pipeline and a locking assembly. The movable pipeline is movably connected to the flow guide pipeline. The locking assembly is in transmission connection with the movable pipeline. The flow guide pipeline is connected to the oxygen generation mechanism. The locking assembly has a locking position and an unlocking position. When the locking assembly is in the locking position, the movable pipeline is clamped to or inserted into an air inlet of the oxygen generation mechanism. When the locking assembly is in the unlocking position, the movable pipeline is separated from the air inlet of the oxygen generation mechanism.

In the household oxygen generator according to the present application, the oxygen generation mechanism includes at least two molecular sieve units. A molecular sieve unit of the at least two molecular sieve units includes a first port and a second port. At least two movable pipelines are provided. Each of the at least two movable pipelines is cooperated with the first port of a respective one of the at least two molecular sieve units. The locking assembly includes an air pipe fixing plate. The air pipe fixing plate is provided with at least two limiting grooves. Each of the at least two movable pipelines is engaged into a respective one of the at least two limiting grooves In an embodiment, the locking assembly includes a fixing seat, a sliding block, a fixing block, a first connection rod and a second connection rod. The sliding block is movably disposed on the fixing seat and is connected to the air pipe fixing plate. The fixing block is fixedly disposed on the fixing seat. Two ends of the first connection rod are hinged to the fixing block and the second connection rod, respectively. The second connection rod is hinged to the sliding block.

In an embodiment, a handle is disposed at a free end of the second connection rod.

In an embodiment, the fixing seat is provided with a first receiving groove. When the locking assembly is in the locking position, the handle is inserted into the first receiving groove.

In an embodiment, a support plate is disposed in the housing. The support plate is located on a side of the oxygen generation mechanism towards the compression mechanism and is provided with a threaded hole. The locking assembly includes a threaded member. The threaded member is connected to the air pipe fixing plate and is inserted through the threaded hole.

In an embodiment, the flow guide pipeline includes a first guide pipe segment. Part of each of the at least two movable pipelines is inserted through the first guide pipe segment, and each of the at least two movable pipelines is movable in an axial direction of the first guide pipe segment. The oxygen generation mechanism includes a second guide pipe segment. The second guide pipe segment communicates with the first port, and each of the at least two movable pipelines may be inserted into or moved out of the second guide pipe segment.

In an embodiment, a first sealing member is sleeved on an outer wall of each of the at least two movable pipelines, and the first sealing member is located in the first guide pipe segment and is abutted against an inner wall of the first guide pipe segment; and/or a second sealing member is sleeved on an outer wall of each of the at least two movable pipelines, and when the locking assembly is in the locking position, the second sealing member is located in the second guide pipe segment and is abutted against an inner wall of the second guide pipe segment.

In an embodiment, a first stop portion is disposed on each of the at least two movable pipelines. The first stop portion is located in the first guide pipe segment. The first sealing member is sleeved on the first stop portion. A third sealing member is also sleeved on each of the at least two movable pipelines. The first guide pipe segment defines a second stop portion. The second stop portion is located on a side of the first stop portion facing the air pipe fixing plate. The third sealing member is clampable between the second stop portion and the first stop portion.

In the household oxygen generator according to the present application, the oxygen generation mechanism includes an adsorbent cylinder, and an axial direction of the first guide pipe segment is perpendicular to an axial direction of the adsorbent cylinder.

The household oxygen generator according to the present application, the oxygen generation mechanism includes an adsorbent cylinder and an adsorbent cover connected to each other. An oxygen generation adsorbent is provided in the adsorbent cylinder. A second receiving groove and a rotatable lifting handle are disposed on the adsorbent cover. The rotatable lifting handle is rotatably to a position where the rotatable lifting handle is inserted into the second receiving groove and a position where the rotatable lifting handle is located outside the second receiving groove.

The above-described technical solutions provided in embodiments of the present application have the following advantages compared with the existing technology. In the household oxygen generator provided in the embodiments of the present application, the compression mechanism is configured to compress air and pressurize the air. The oxygen generation mechanism is configured to adsorb and filter the compressed air to generate high concentration of oxygen. The first air path module is connected to the compression mechanism and the oxygen generation mechanism to import the compressed air from the compression mechanism into the oxygen generation mechanism. During the assembling of the household oxygen generator, when the oxygen generation mechanism is assembled into the housing, the locking assembly is in the unlocked position to avoid the oxygen generation mechanism, thereby facilitating the assembly of various components. In this case, the locking assembly is moved to make the locking assembly in the locked position, and the movable pipeline is engaged into or inserted into the air inlet of the oxygen generation mechanism, so that the first air path module communicates with the oxygen generation mechanism. Alternatively, after the oxygen generation mechanism has been used in long-term operation, the oxygen generation adsorbent will gradually become ineffective. When the oxygen generation adsorbent needs to be replaced, the locking assembly is moved to the unlocking position to separate the movable pipeline from the air inlet of the oxygen generation mechanism, thereby facilitating the disassembly of the oxygen generation mechanism. In this way, the movable pipeline is provided, and the position of the movable pipeline is changed by using the locking assembly to achieve the assembly and disassembly between the movable pipeline and the oxygen generation mechanism, thereby reducing the difficulty of communicating the oxygen generation mechanism with and disassembling the oxygen generation mechanism from the first air path module, and facilitating the use for non-professionals.

BRIEF DESCRIPTION OF DRAWINGS

The drawings herein, which are incorporated into and constitute a part of this specification, show embodiments conforming to the present utility model, and are used together with the specification to explain the principles of the present utility model.

In order to more clearly illustrate the technical solutions in the embodiments of the present utility model or in the existing technology, the drawings used in the description of the embodiments or the existing technology will be briefly introduced below. Obviously, for those of ordinary skill in the art, other drawings may also be obtained without requiring creative efforts according to these drawings.

Figure 1:
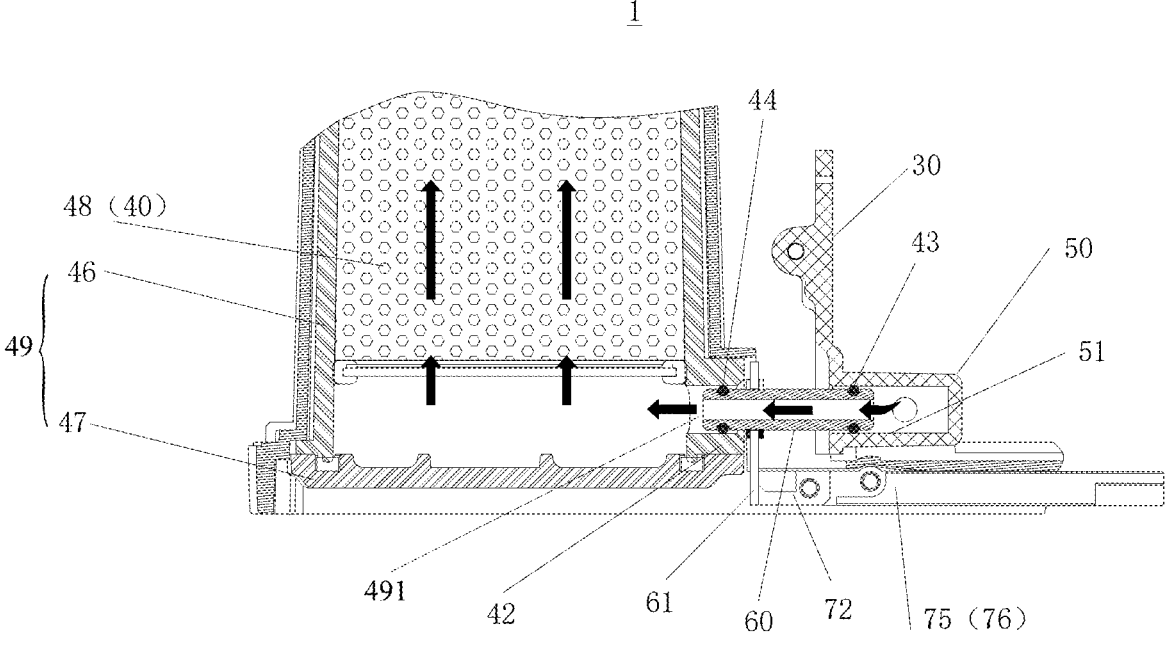

One or more embodiments are exemplarily illustrated by the images in the drawings corresponding to the one or more embodiments. These exemplary illustrations do not limit the embodiments. Elements with the same reference numerals in the drawings represent similar elements. Unless otherwise stated, figures in the drawings do not constitute a limitation of proportion.

Figure 2:
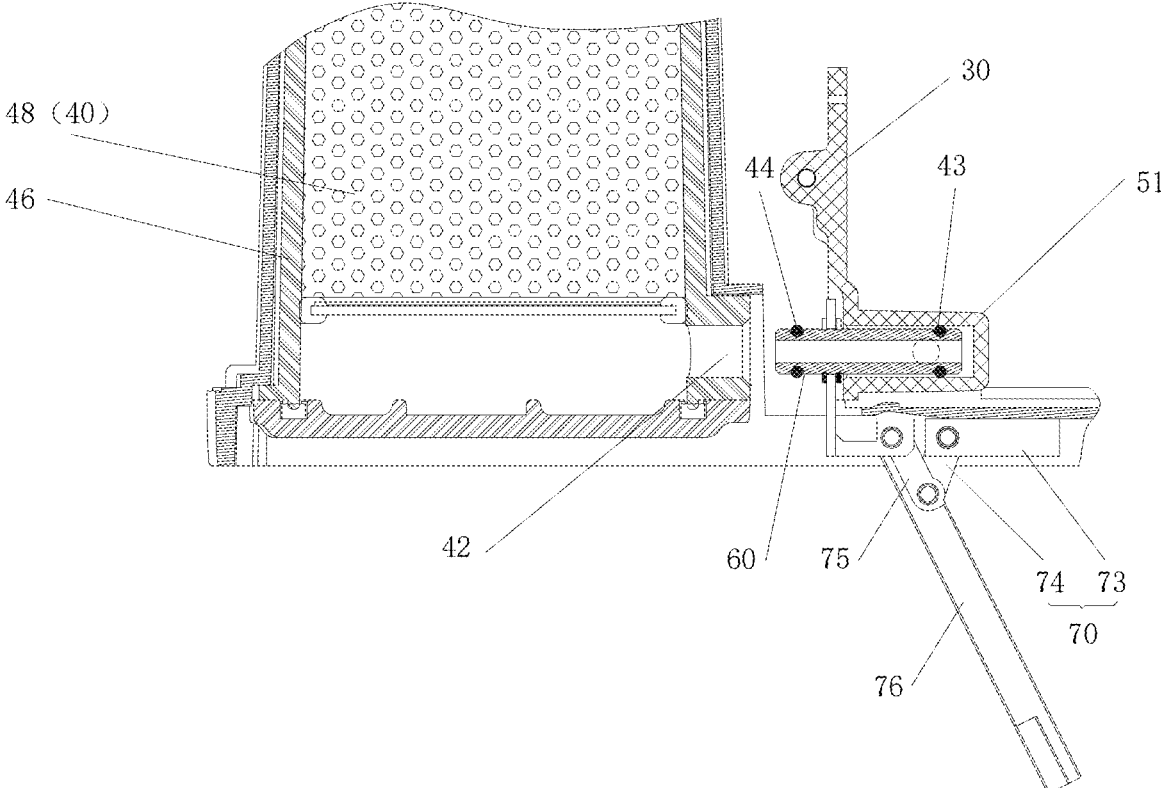
Figure 3:
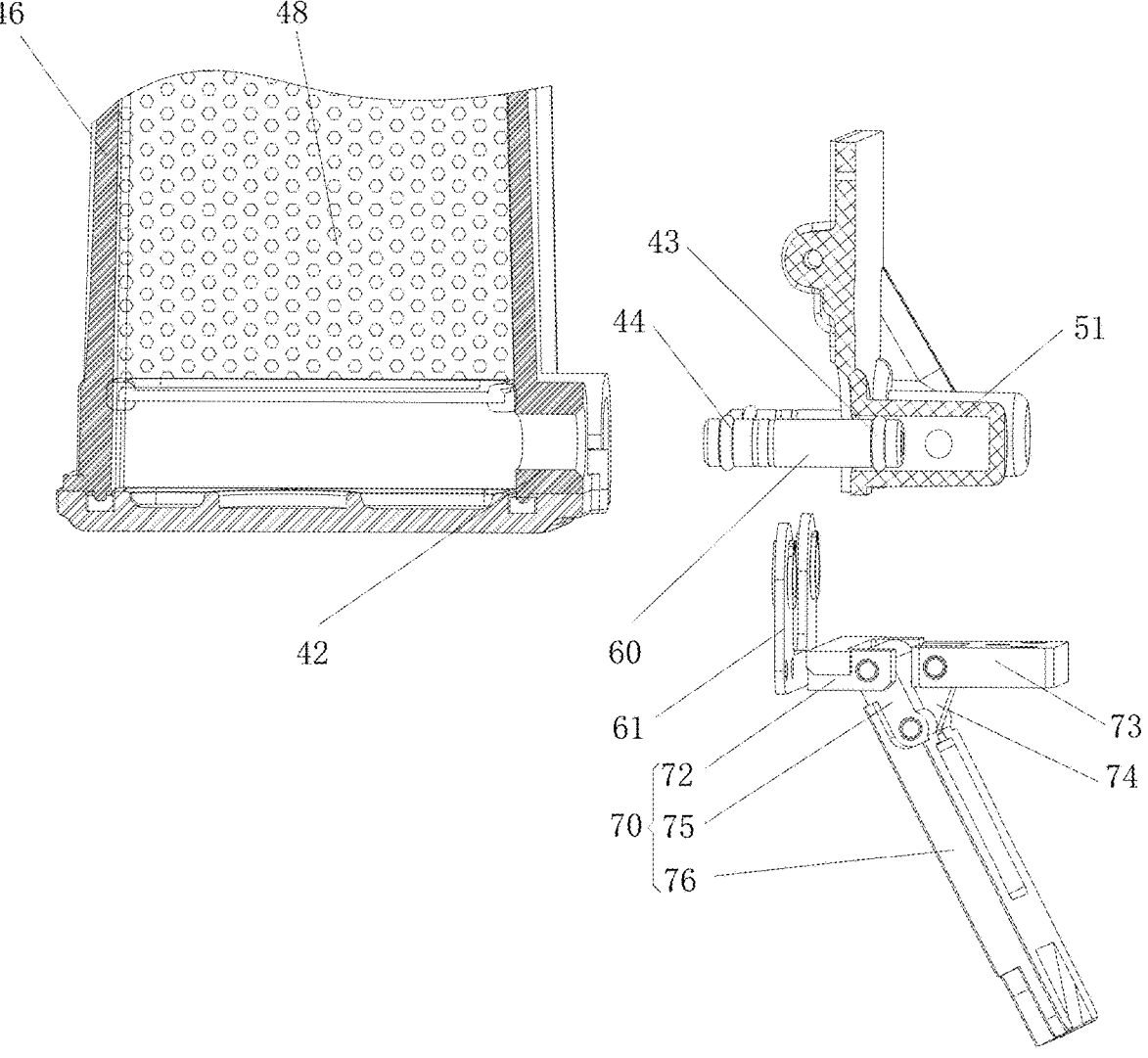
Figure 4:
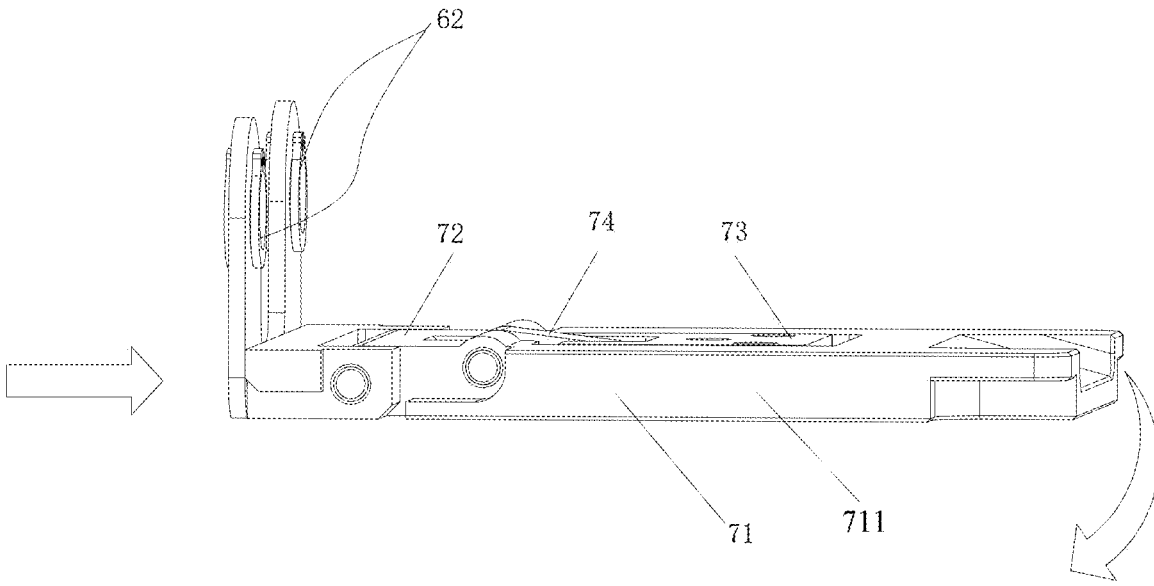
Figure 5:
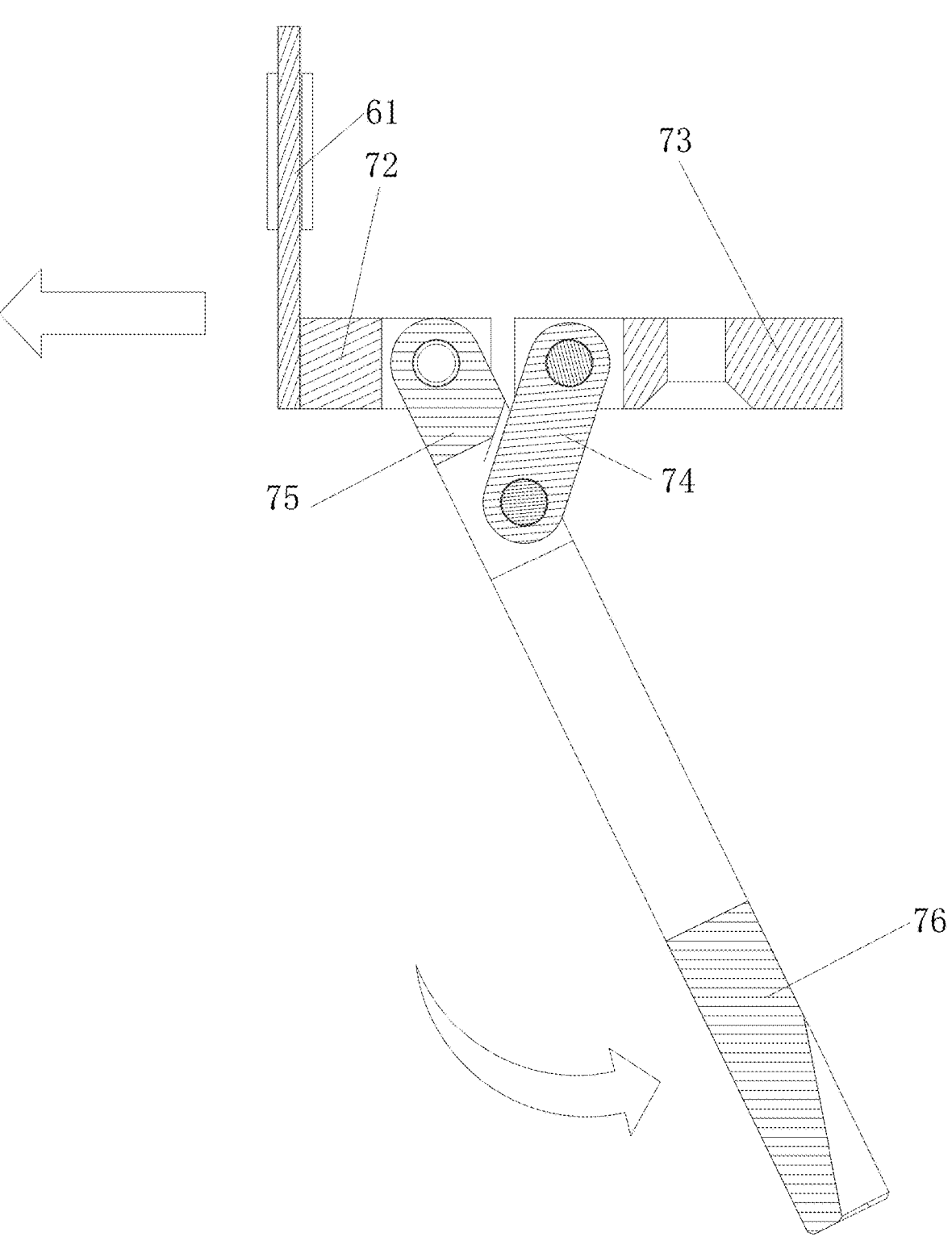
Figure 6:
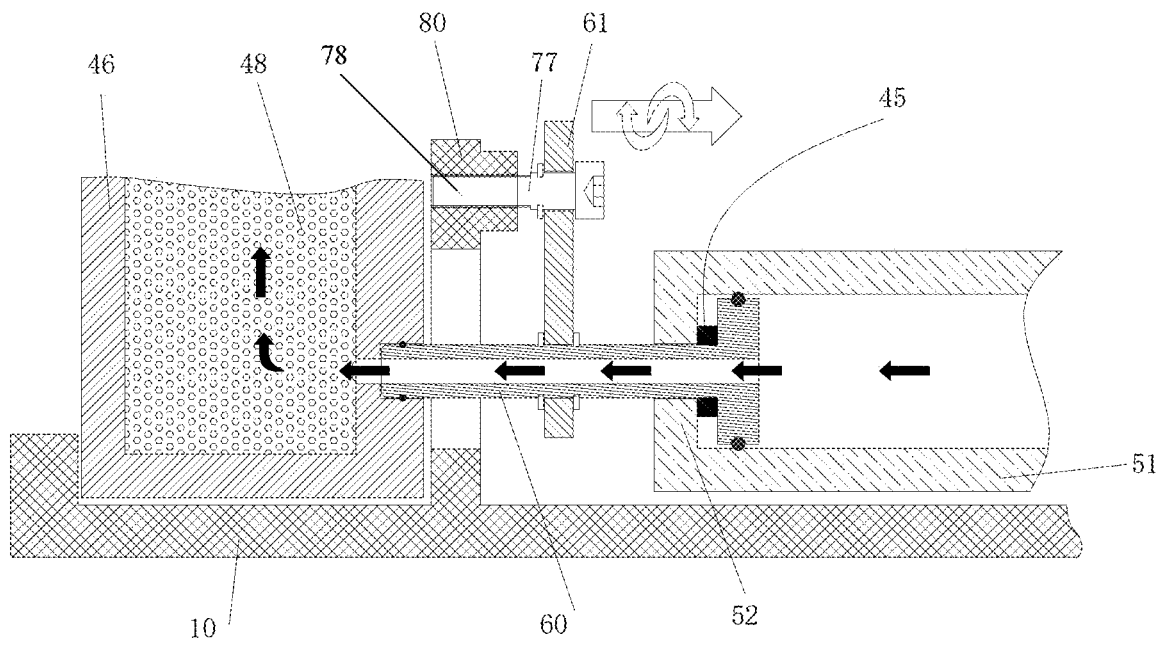
Figure 7:
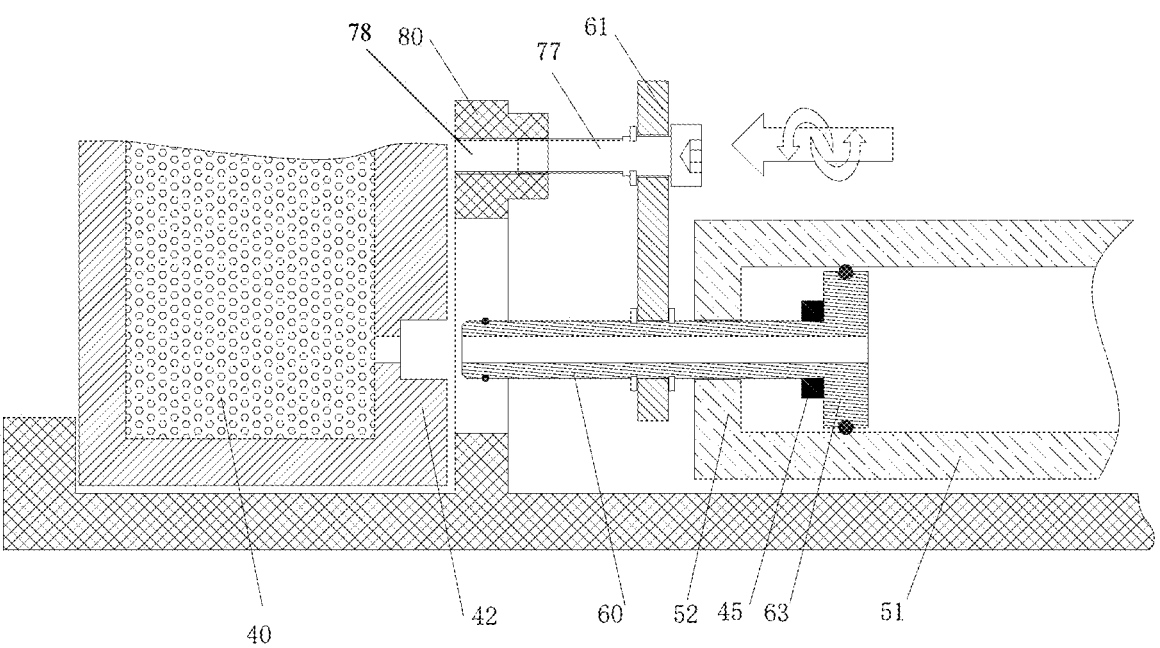

FIG. 1 is a partial sectional view of a locking position of a household oxygen generator according to an embodiment one of the present application:

FIG. 2 is a partial sectional view of an unlocking position of a household oxygen generator according to an embodiment one of the present application;

FIG. 3 is an exploded view of a household oxygen generator according to an embodiment one of the present application;

FIG. 4 is a perspective view of a locking assembly of a household oxygen generator according to an embodiment one of the present application;

FIG. 5 is a sectional view of a locking assembly of a household oxygen generator according to an embodiment one of the present application;

FIG. 6 is a sectional view of a locking position of a household oxygen generator according to an embodiment two of the present application; and FIG. 7 is a sectional view of an unlocking position of a household oxygen generator according to an embodiment two of the present application.

LIST OF REFERENCE NUMBERS

1 household oxygen generator
10 housing
30 first air path module
40 oxygen generation mechanism
42 second guide pipe segment
43 first sealing member
44 second sealing member
45 third sealing member
46 adsorbent cylinder
47 adsorbent cover
48 oxygen generation adsorbent
49 molecular sieve unit
491 first port
50 flow guide pipeline
51 first guide pipe segment
52 second stop portion
60 movable pipeline
61 air pipe fixing plate
62 limiting groove
63 first stop portion
70 locking assembly
71 fixing seat
711 first receiving groove
72 sliding block
73 fixing block
74 first connection rod
75 second connection rod
76 handle
77 threaded member
78 threaded hole
80 support plate

DETAILED DESCRIPTION

In order to make the objectives, technical solutions, and advantages of embodiments of the present application clearer, the technical solutions of the embodiments of the present application will be clearly and fully described below in conjunction with the drawings of the embodiments of the present application. Apparently, the described embodiments are merely part of the embodiments of the present application, rather than all of the embodiments of the present application. All other embodiments obtained by those of ordinary skill in the art based on the embodiments of the present application without requiring creative efforts shall all fall within the scope of protection of the present application.

The following disclosure provides many different embodiments or examples for implementing different structures of the present utility model. In order to simplify the disclosure of the present utility model, components and arrangements of examples are described below. Of course, they are only examples and are not intended to limit the present utility model. In addition, the present utility model may repeat reference numerals and/or letters in different examples. This repetition is for the purpose of simplicity and clarity and does not in itself indicate the relationship between the various embodiments and/or arrangements discussed.

For ease of description, spatial relative terms may be used herein to describe the relative positional relationships or movement condition of one element or feature shown in the drawings with respect to another element or feature. Such relative terms include, for example, "inside", "outside", "inner side", "outer side", "beneath", "below", "over", "above", "front", "rear" and the like. These spatial relative terms are intended to include different orientations of the apparatus in use or operation, in addition to the orientations depicted in the drawings. For example, if the apparatus in the drawings undergoes a position reversal, a change in attitude, or a change in a motion state, then these directional indications will change accordingly. For example, an element described as "beneath" or "below" other elements or features will subsequently be oriented as "over" or "above" other elements or features. Thus, the exemplary term "below" may encompass both upward and downward orientations. The apparatus may be oriented otherwise (rotated 90 degrees or in other directions), and the spatial relative descriptors used herein should be interpreted accordingly.

As shown in FIG. 1 to FIG. 6, a household oxygen generator 1 according to the embodiments of the present application includes a housing 10. A compression mechanism, a first air path module 30 and an oxygen generation mechanism 40 which are communicated in sequence are disposed in the housing 10. The first air path module 30 includes a flow guide pipeline 50, a movable pipeline 60 and a locking assembly 70. The movable pipeline 60 is movably connected to the flow guide pipeline 50. The locking assembly 70 is in transmission connection with the movable pipeline 60. The flow guide pipeline 50 is connected to the oxygen generation mechanism 40. The locking assembly 70 has a locking position and an unlocking position. When the locking assembly 70 is in the locking position, the movable pipeline 60 is engaged into or inserted into an air inlet of the oxygen generation mechanism 40. When the locking assembly 70 is in the unlocking position, the movable pipeline 60 is separated from the air inlet of the oxygen generation mechanism 40.

The compression mechanism is configured to compress air and pressurize the air. The oxygen generation mechanism 40 is configured to adsorb and filter the compressed air to generate high concentration of oxygen. The first air path module 30 is connected to the compression mechanism and the oxygen generation mechanism 40 to import the compressed air from the compression mechanism into the oxygen generation mechanism 40. During the assembling of the household oxygen generator 1, when the oxygen generation mechanism 40 is assembled into the housing 10, the locking assembly 70 is in the unlocked position to avoid the oxygen generation mechanism 40, thereby facilitating the assembly of various components. In this case, the locking assembly 70 is moved to make the locking assembly 70 in the locked position, and the movable pipeline 60 is engaged into or inserted into the air inlet of the oxygen generation mechanism 40, so that the first air path module 30 communicates with the oxygen generation mechanism 40. Alternatively, after the oxygen generation mechanism 40 has been used in long-term operation, an oxygen generation adsorbent 48 in the oxygen generation mechanism 40 will gradually become ineffective. When the oxygen generation adsorbent 48 needs to be replaced, the locking assembly 70 is moved to the unlocking position to separate the movable pipeline 60 from the air inlet of the oxygen generation mechanism 40, thereby facilitating the disassembly of the oxygen generation mechanism 40.

The movable pipeline 60 is engaged into or inserted into the air inlet of the oxygen generation mechanism 40. That is to say, in some embodiments, the movable pipeline 60 is engaged into the air inlet of the oxygen generation mechanism 40. It is to be understood that, even if the movable pipeline 60 is engaged into the air inlet of the oxygen generation mechanism 40, the movable pipeline 60 may be moved to be disconnected from the oxygen generation mechanism 40 during the movement of the locking assembly 70. In some embodiments, the movable pipeline 60 is inserted into the oxygen generation mechanism 40.

According to the household oxygen generation machine 1 of the embodiments of the present application, the movable pipeline 60 is provided, and the position of the movable pipeline 60 is changed by using the locking assembly 70 to achieve the assembly and disassembly between the movable pipeline 60 and the oxygen generation mechanism 40, thereby reducing the difficulty of communicating the oxygen generation mechanism 40 with and disassembling the oxygen generation mechanism from the first air path module 30, and facilitating the use for non-professionals.

In some embodiments, the oxygen generation mechanism 40 includes at least two molecular sieve units 49. A molecular sieve unit 49 of the at least two molecular sieve units 49 includes a first port 491 and a second port. The air inlet of the oxygen generation mechanism 40 communicates with the first ports 491 of the at least two molecular sieve units 49 simultaneously. An air outlet of the oxygen generation mechanism 40 communicates with the second ports of the at least two molecular sieve units 49 simultaneously. In this way, the molecular sieve units 49 in the oxygen generation mechanism 40 simultaneously intake air, simultaneously discharge air, and simultaneously generate oxygen.

As shown in FIG. 1 and FIG. 4, according to the household oxygen generator 1 of the embodiments of the present application, the oxygen generation mechanism 40 includes at least two molecular sieve units 49. A molecular sieve unit of the at least two molecular sieve units 49 includes a first port 491 and a second port. At least two movable pipelines 60 are provided. Each of the at least two movable pipelines 60 is cooperated with the first port 491 of a respective one of the at least two molecular sieve units 49. The locking assembly 70 includes an air pipe fixing plate 61. The air pipe fixing plate 61 is provided with at least two limiting grooves 62, and each of the at least two movable pipelines 60 is engaged into a respective one of the at least two limiting grooves 62.

In other words, the movable pipelines 60 is cooperated with the molecular sieve units 49 in one-to-one correspondence, so that the molecular sieve units may be independently controlled to generate oxygen. For example, when one molecular sieve unit 49 of the molecular sieve units 49 is generating oxygen, the corresponding movable pipeline 60 provides compressed air for the one molecular sieve unit 49, concentrated oxygen generated by the one molecular sieve unit 49 is discharged from the second port, part of the concentrated oxygen enters an oxygen storage mechanism and finally provides oxygen for users, part of the concentrated oxygen enters through the second port of another molecular sieve unit 49 to perform an exhaust air washing on another molecular sieve unit 49, and the exhaust air is discharged from the first port 491 of the another molecular sieve unit 49 and from the movable line 60 connected to the first port 491 of another molecular sieve unit 49.

In an embodiment, the molecular sieve unit 49 includes the first port 491 and the second port which are opposite to each other in a length direction, the first port 491 is disposed at the bottom of the molecular sieve unit 49, and the second port is disposed at the top of the molecular sieve unit 49.

As shown in FIG. 3 to FIG. 5, in some embodiments, the locking assembly 70 includes a fixing seat 71, a sliding block 72, a fixing block 73, a first connection rod 74 and a second connection rod 75. The sliding block 72 is movably disposed on the fixing seat 71 and is connected to the air pipe fixing plate 61. The fixing block 73 is fixedly disposed on the fixing seat 71. Two ends of the first connection rod 74 are hinged to the fixing block 73 and the second connection rod 75, respectively, and the second connection rod 75 is hinged to the sliding block 72.

The locking assembly 70 includes the fixing seat 71, the sliding block 72, the fixing block 73, the first connection rod 74 and the second connection rod 75. The sliding block 72 is movably disposed on the fixing seat 71, that is to say, the sliding block 72 is movable. The fixing block 73 is fixedly disposed on the fixing seat 71. Two ends of the first connection rod 74 are hinged to the fixing block 73 and the second connection rod 75, respectively, and the second connection rod 75 is hinged to the sliding block 72. During the rotation of the second connection rod 75, since the fixing block 73 remains stationary, as the first connection rod 74 rotates, the first connection rod 74 simultaneously pushes the second connection rod 75 to move, the second connection rod 75 is moved to drive the sliding block 72 to move, thereby finally driving the air pipe fixing plate 61 to move.

The fixing seat 71 has functions of limiting and guiding the sliding block 72, so that the sliding block 72 moves along a predetermined trajectory.

As shown in FIG. 3, in some embodiments, a handle 76 is disposed at a free end of the second connection rod 75. In this way, it is convenient for users to directly grip the handle 76 and drive the second connection rod 75 to rotate, thereby finally driving the air pipe fixing plate 61 to move.

In some embodiments, the fixing seat 71 is provided with a first receiving groove 711. When the locking assembly 70 is in the locking position, the handle 76 is inserted into the first receiving groove 711. With this arrangement, the first receiving groove 711 is configured to receive the handle 76, so that the overall volume of the locking assembly 70 during assembly is reduced, the space occupied in the housing 10 is reduced, and further the overall volume of the household oxygen generator 1 is reduced.

In some embodiments, an avoidance groove is disposed at an end of the handle 76 facing away from the second connection rod 75. When the handle 76 is inserted into the first receiving groove 711, the avoidance groove is opposite to the bottom wall of the first receiving groove 711, an avoidance space is defined by a free end of the handle 76 and a side wall of the first receiving groove 711, and the avoidance space communicates with the first receiving groove 711. With this arrangement, it is convenient for fingers to extend into the handle 76 in the first receiving groove 711 via the avoidance space to apply forces, so that the handle 76 is moved out of the first receiving groove 711.

As shown in FIGS. 6 and 7, in some embodiments, a support plate 80 is disposed in the housing 10. The support plate 80 is located on a side of the oxygen generation mechanism 40 facing the compression mechanism and is provided with a threaded hole 78. The locking assembly 70 includes a threaded member 77. The threaded member 77 is connected to the air pipe fixing plate 61 and is inserted through the threaded hole 78.

The threaded member 77 is inserted through the threaded hole 78, and the threaded member 77 is connected to the air pipe fixing plate 61. When the threaded member 77 is rotated, the threaded member 77 will gradually approach or move away from the support plate 80 along engaged threads, so that the air pipe fixing plate 61 is driven to move by rotating the threaded member 77.

As shown in FIGS. 1 to 3, FIG. 6 and FIG. 7, in some embodiments, the flow guide pipeline 50 includes a first guide pipe segment 51. Part of the movable pipeline 60 is inserted through the first guide pipe segment 51, and the movable pipeline 60 may move in an axial direction of the first guide pipe segment 51. The oxygen generation mechanism 40 includes a second guide pipe segment 42, the second guide pipe segment 42 communicates with the first port 491, and the movable pipeline 60 may be inserted into or moved out of the second guide pipe segment 42.

The part of the movable pipeline 60 is always inserted through the first guide pipe segment 51, and the difference lies in that when the movable pipeline 60 is located at different positions, lengths of the movable pipeline 60 being inserted into the first guide pipe segment 51 are different. In this way, except that the first guide pipe segment 51 communicates with the movable pipeline 60, the first guide pipe segment 51 also has the effect of guiding the movable pipeline 60, so that the movable pipeline 60 is always moved in the axial direction of the first guide pipe segment 51 during movement, in this case, the movable pipeline 60 always move along a predetermined trajectory during movement. With the movement of the locking assembly 70, the movable pipeline 60 is driven to be inserted into or moved out of the second guide pipe segment 42, the second guide pipe segment 42, apart from having the function of communicating with the movable pipeline 60, also guide the other end of the movable pipeline 60, as the movable pipeline 60 is moved out of the first guide pipe segment 51, the movable pipe segment is kept balanced and moves along the predetermined trajectory under the guiding action of the second guide pipe segment 42.

As shown in FIGS. 1 and 2, in some embodiments, a first sealing member 43 is sleeved on an outer wall of the movable pipeline 60, and the first sealing member 43 is located in the first guide pipe segment 51 and is abutted against an inner wall of the first guide pipe segment 51.

It is to be understood that, the movable pipeline 60 is configured to transmit gas. Since the movable pipeline 60 is movable, the first sealing member 43 is disposed on the movable pipeline 60 so that the air tightness between the movable pipeline 60 and the first guide pipe segment 51 can be enhanced, and thus the air leakage can be prevented.

As shown in FIGS. 1 and 2, in some embodiments, a second sealing member 44 is sleeved on an outer wall of the movable pipeline 60. When the locking assembly 70 is in the locking position, the second sealing member 44 is located in the second guide pipe segment 42 and is abutted against an inner wall of the second guide pipe segment 42.

The movable pipeline 60 is configured to transmit a gas. Since the movable pipeline 60 is movable, the second sealing member 44 is sleeved on the outer wall of the movable pipeline 60, when the locking assembly 70 is in the locking position, the second sealing member 44 is located in the second guide pipe segment 42 and is abutted against the inner wall of the second guide pipe segment 42, thereby the air tightness between the movable pipeline 60 and the second guide pipe segment 42 is enhanced by using the second sealing member 44, and thus the air leakage can be prevented.

As shown in FIG. 6 and FIG. 7, in some embodiments, a first stop portion 63 is disposed on the movable pipeline 60. The first stop portion 63 is located in the first guide pipe segment 51. The first sealing member 43 is sleeved on the first stop portion 63, and a third sealing member 45 is also sleeved on the movable pipeline 60. The first guide pipe segment 51 defines a second stop portion 52. The second stop portion 52 is located on a side of the first stop portion 63 facing the air pipe fixing plate 61, and the third sealing member 45 is clampable between the second stop portion 52 and the first stop portion 63.

The second stop portion 52 is located on a side of the first stop portion 63 facing the air pipe fixing plate 61. The second stop portion 52 may block the first stop portion 63 to prevent the movable pipeline 60 from disengaging from the first guide pipe segment 51, thereby playing a role in guiding and limiting. When the first stop portion 63 is moved until the first sealing member 43 is abutted against and stopped by the second stop portion 52, the third sealing member 45 is clamped between the first stop portion 63 and the second stop portion 52, thereby further improving the air tightness between the movable pipeline 60 and the first guide pipe segment 51.

According to the household oxygen generator 1 of the embodiments of the present application, the oxygen generation mechanism includes an adsorbent cylinder 46, and the axial direction of the first guide pipe segment 51 is perpendicular to an axial direction of the adsorbent cylinder 46. With this arrangement, it is convenient to conduct positioning and calibration, thereby enabling positions of various mechanisms to be set more reasonably and simplifying the difficulty of positioning and calibration.

According to the household oxygen generator 1 of the embodiments of the present application, the oxygen generation mechanism 40 includes an adsorbent cover 47. The adsorbent cover 47 is connected to the adsorbent cylinder 46. The oxygen generation adsorbent 48 is provided in the adsorbent cylinder 46, and a second receiving groove and a rotatable lifting handle are disposed on the adsorbent cover 47. The rotatable lifting handle is rotatably to a position where the rotatable lifting handle is inserted into the second receiving groove and a position where the rotatable lifting handle is located outside the second receiving groove.

The oxygen generation adsorbent 48 is provided in the adsorbent cylinder 46, an adsorbent pressure plate is disposed above the adsorbent cover 47, and a spring is sandwiched between the adsorbent pressure plate and the adsorbent cover 47. The spring is in a compressed state, so that the oxygen generation adsorbent 48 is always in a tight-compressed state, and thus the efficient air separation is ensured.

In some embodiments, a first adsorbent sheet is provided in the adsorbent cylinder 46. Since the oxygen generation adsorbent 48 will be pulverized during use, a particle size of the pulverized molecular sieve is relatively small, in this case, the first adsorbent filter sheet is provided to enable the adsorbent to be filtered, thereby improving the cleanliness of oxygen.

It is to be understood that the terms used herein are only for the purpose of describing exemplary embodiments and are not intended to be limiting. Unless the context clearly indicates otherwise, singular forms such as "a", "an", and "the" as used herein may also represent including plural forms. The terms "include", "comprise", "contain", and "have" are inclusive, and thus indicate the existence of the stated features, steps, operations, elements, and/or components, but do not preclude the existence or addition of one or more other features, steps, operations, elements, components, and/or combinations thereof. The method steps, processes, and operations described herein are not to be construed as necessarily requiring them to be performed in the specific order described or illustrated, unless the order of execution is clearly specified. It is also to be understood that additional or alternative steps may be used.

Although terms such as first, second, third may be used herein to describe multiple elements, components, regions, layers and/or segments, these elements, components, regions, layers and/or segments should not be limited by these terms. These terms may only be used to distinguish one element, one component, one region, one layer or one segment from another region, another layer or another segment. Unless clearly indicated by the context, terms such as "first", "second" and other numerical terms, when used herein, do not imply order or sequence. Therefore, a first element, a first component, a first region, a first layer or a first segment discussed below could be referred to as a second element, a second component, a second region, a second layer or a second segment without departing from the teachings of the exemplary embodiments.

The above contents are merely the exemplary embodiments of the present utility model, to enable those skilled in the art to understand or implement the present utility model. Various modifications to these embodiments will be apparent to those skilled in the art. The general principles defined herein may be implemented in other embodiments without departing from the spirit or scope of the present utility model. Therefore, the present utility model will not be limited to the embodiments shown herein, but should be accorded the broadest scope consistent with the principles and novel features disclosed herein.

What is claimed is:

1. A household oxygen generator, comprising a housing, wherein a compression mechanism, a first air path module and an oxygen generation mechanism which are communicated in sequence are disposed in the housing, the first air path module comprises a flow guide pipeline, a movable pipeline and a locking assembly, the movable pipeline is movably connected to the flow guide pipeline, the locking assembly is in transmission connection with the movable pipeline, the flow guide pipeline is connected to the oxygen generation mechanism, the locking assembly has a locking position and an unlocking position, when the locking assembly is in the locking position, the movable pipeline is engaged into or inserted into an air inlet of the oxygen generation mechanism, and when the locking assembly is in the unlocking position, the movable pipeline is separated from the air inlet of the oxygen generation mechanism.

2. The household oxygen generator of claim 1, wherein the oxygen generation mechanism comprises at least two molecular sieve units, a molecular sieve unit of the at least two molecular sieve units comprises a first port and a second port, at least two movable pipelines are provided, each of the at least two movable pipelines is cooperated with the first port of a respective one of the at least two molecular sieve units, the locking assembly comprises an air pipe fixing plate, the air pipe fixing plate is provided with at least two limiting grooves, and each of the at least two movable pipelines is engaged into a respective one of the at least two limiting grooves.

3. The household oxygen generator of claim 2, wherein the locking assembly comprises a fixing seat, a sliding block, a fixing block, a first connection rod and a second connection rod, the sliding block is movably disposed on the fixing seat and is connected to the air pipe fixing plate, the fixing block is fixedly disposed on the fixing seat, two ends of the first connection rod are hinged to the fixing block and the second connection rod, respectively, and the second connection rod is hinged to the sliding block.

4. The household oxygen generator of claim 3, wherein a handle is disposed at a free end of the second connection rod.

5. The household oxygen generator of claim 4, wherein the fixing seat is provided with a first receiving groove, and when the locking assembly is in the locking position, the handle is inserted into the first receiving groove.

6. The household oxygen generator of claim 2, wherein a support plate is disposed in the housing, the support plate is located on a side of the oxygen generation mechanism facing the compression mechanism and is provided with a threaded hole, the locking assembly comprises a threaded member, and the threaded member is connected to the air pipe fixing plate and is inserted through the threaded hole.

7. The household oxygen generator of claim 2, wherein the flow guide pipeline comprises a first guide pipe segment, part of each of the at least two movable pipelines is inserted through the first guide pipe segment, each of the at least two movable pipelines is movable in an axial direction of the first guide pipe segment, the oxygen generation mechanism comprises a second guide pipe segment, the second guide pipe segment communicates with the first port, and each of the at least two movable pipelines may be inserted into or removed from the second guide pipe segment.

8. The household oxygen generator of claim 7, wherein a first sealing member is sleeved on an outer wall of each of the at least two movable pipelines, and the first sealing member is located in the first guide pipe segment and is abutted against an inner wall of the first guide pipe segment.

9. The household oxygen generator of claim 8, wherein a first stop portion is disposed on each of the at least two movable pipelines, the first stop portion is located in the first guide pipe segment, the first sealing member is sleeved on the first stop portion, a third sealing member is also sleeved on each of the at least two movable pipelines, the first guide pipe segment defines a second stop portion, the second stop portion is located on a side of the first stop portion facing the air pipe fixing plate, and the third sealing member is clampable between the second stop portion and the first stop portion.

10. The household oxygen generator of claim 7, wherein the oxygen generation mechanism comprises an adsorbent cylinder, and an axial direction of the first guide pipe segment is perpendicular to an axial direction of the adsorbent cylinder.

11. The household oxygen generator of claim 1, wherein the oxygen generation mechanism comprises an adsorbent cylinder and an adsorbent cover connected to each other, an oxygen generation adsorbent is provided in the adsorbent cylinder, a second receiving groove and a rotatable lifting handle are disposed on the adsorbent cover, and the rotatable lifting handle is rotatable between a position where the rotatable lifting handle is inserted into the second receiving groove and a position where the rotatable lifting handle is located outside the second receiving groove.

12. The household oxygen generator of claim 7, wherein a second sealing member is sleeved on an outer wall of each of the at least two movable pipelines, and when the locking assembly is in the locking position, the second sealing member is located in the second guide pipe segment and is abutted against an inner wall of the second guide pipe segment.

13. The household oxygen generator of claim 7, wherein a first sealing member is sleeved on an outer wall of each of the at least two movable pipelines, and the first sealing member is located in the first guide pipe segment and is abutted against an inner wall of the first guide pipe segment; and a second sealing member is sleeved on an outer wall of each of the at least two movable pipelines, and when the locking assembly is in the locking position, the second sealing member is located in the second guide pipe segment and is abutted against an inner wall of the second guide pipe segment.

14. The household oxygen generator of claim 8, wherein the oxygen generation mechanism comprises an adsorbent cylinder, and an axial direction of the first guide pipe segment is perpendicular to an axial direction of the adsorbent cylinder.

15. The household oxygen generator of claim 9, wherein the oxygen generation mechanism comprises an adsorbent cylinder, and an axial direction of the first guide pipe segment is perpendicular to an axial direction of the adsorbent cylinder.

* * * * *